United States Patent [19]

Ushiyama

[11] 4,447,206
[45] May 8, 1984

[54] DEVICE AND METHOD FOR DETECTING APICAL CONSTRICTION IN ROOT CANAL OF TOOTH

[76] Inventor: Junji Ushiyama, 5829-761, Kamishin-ei-cho, Niigata-shi, Niigata-ken, Japan

[21] Appl. No.: 454,873

[22] Filed: Dec. 30, 1982

[30] Foreign Application Priority Data

Jan. 18, 1982 [JP] Japan .................................. 57-6420
Jan. 18, 1982 [JP] Japan .................................. 57-6421

[51] Int. Cl.³ .............................................. A61C 3/00
[52] U.S. Cl. ...................................... 433/27; 433/32; 433/72; 128/776; 73/304 R; 324/64
[58] Field of Search ...................... 433/27, 32, 72, 224; 128/734, 735, 776, 777, 738, 639, 640, 641, 642, 643, 644; 73/304 R, 304 C; 324/64, 158 P

[56] References Cited

U.S. PATENT DOCUMENTS

| | | | |
|---|---|---|---|
| 2,763,935 | 9/1956 | Whaley et al. | 128/734 |
| 2,786,661 | 3/1957 | Herzog et al. | 324/64 |
| 2,838,731 | 6/1958 | Cruzan et al. | 324/64 |
| 3,131,335 | 4/1964 | Berglund et al. | 73/304 R |
| 3,365,663 | 1/1968 | Yamaguchi | 324/64 |
| 3,866,600 | 2/1975 | Rey | 128/734 |
| 4,101,827 | 7/1978 | Offner | 324/64 |
| 4,193,408 | 3/1980 | Fujino | 433/27 |
| 4,240,443 | 12/1980 | Ionescu | 128/734 |
| 4,312,360 | 1/1982 | Conway et al. | 128/738 |
| 4,337,038 | 6/1982 | Saito et al. | 433/32 |

OTHER PUBLICATIONS

"Endodontics", 2nd Edition, pp. 184–189, 1976, published by Lea & Febiger, Philadelphia.
"Endodontic Practice", 9th Edition, pp. 208–210, 1978, published by Lea & Febiger, Philadelphia.

*Primary Examiner*—John J. Wilson
*Attorney, Agent, or Firm*—Eugene E. Geoffrey, Jr.

[57] ABSTRACT

A novel and improved system is provided for detecting the apical constriction in the root canal of a tooth, in which the root canal, from which the dental pulp has been removed, is filled with electrolyte solution, a first electrode is put in contact with the mucous membrane in the oral cavity, a second electrode is put in the root canal, a fixed voltage or current is applied between the first and second electrodes, and a third electrode having an insulating coating except for the tip thereof is inserted into the root canal to detect sudden change in the potential along the root canal, and this change is visually and/or audibly indicated to indicate the apical constriction.

9 Claims, 11 Drawing Figures

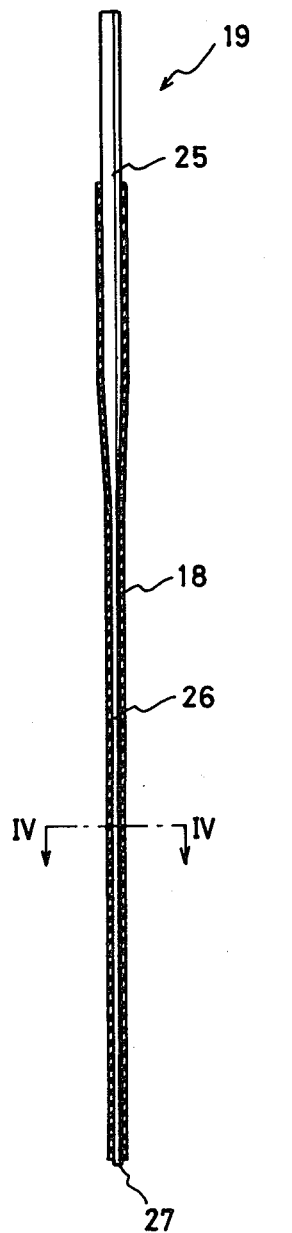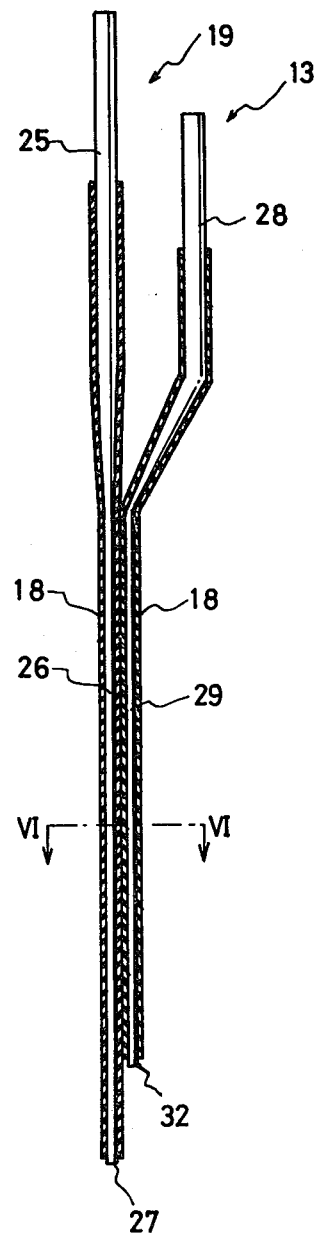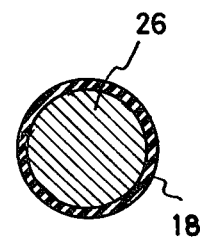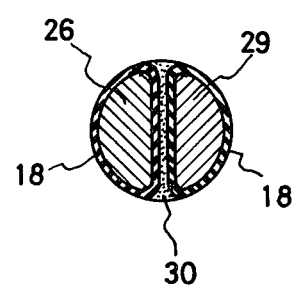
FIG. 3  FIG. 5
FIG. 4
FIG. 6

DEVICE AND METHOD FOR DETECTING APICAL CONSTRICTION IN ROOT CANAL OF TOOTH

This invention relates to a novel device for electrically detecting the apical constriction in the root canal of a decayed tooth, the pulp of which has been removed.

As well known in the art, when tooth decay progresses and a lesion forms in the tooth pulp, it is necessary to remove the pulp, expand mechanically the root canal with a reamer or the like, clean and sterilize it chemically and, then, fill it with a suitable material. Such treatment is applied within a range to the apical constriction which is the portion of the root canal having the least inner diameter near the end of the root of the tooth. While the treatment should be applied within this range without leaving any untreated portion, it must not be applied beyond the apical constriction. Therefore, it is essential to know the precise length of the root canal or position of the apical constriction prior to the treatment of the root canal, and such parameters have been measured in the following manners, as disclosed, for example, in J. I. Ingle and E. E. Beveridge, "Endodontics", 2nd edition, pp. 184–189, published by Lea & Febiger, Philadelphia, in 1976 and L. I. Grossman, "Endodontic Practice", 9th edition, pp. 208–210, published by Lea & Febiger, Philadelphia, in 1978, which are cited herein as references.

1. Method of Digital Tactile Sense

Inserting a thin metal stylet or probe into the root canal, the position of apical constriction is detected through feeling or sense of the operator's fingers. With this method, however, correct measurement cannot be expected since it is liable to be influenced by differences in the shape of apical portion and the operator's feeling.

2. Radiographic Method

An X-ray photograph is taken as a stylet is inserted in the root canal and the lengths of the root of the tooth and the stylet are compared on the photograph to obtain the position of the apical constriction. With this method, however, it is difficult to distinguish where the apical foramen opens, and error of measurement may occur when the apical foramen opens in a position remote from the root apex. Moreover, if the angle of projection of an X-ray is inadequate, the rates of projection of the root of the tooth and the stylet on the film may differ from each other and cause error of measurement. Furthermore, it is believed that the eyeball is very sensitive to X-radiation and a relatively small amount of X-ray exposure may result in an X-ray cataract.

3. Electronic Method Based on the Resistance Determination

This method, wherein electric resistance between a reamer inserted into the root canal and an electrode attached to the gum is measured, is based upon the fact that this electric resistance exhibits a substantially fixed value regardless of age, sex and type of tooth when the reamer tip reaches the apical foramen under a specific condition. However, it is difficult to maintain the condition of measurement always constant in spite of variation in apical foramen diameter, status of tissue exudate, blood, pus and the like, size of reamer and electrochemical property of its surface, and large errors of measurement such as 4 to 5 millimeters may happen occasionally.

Accordingly, an object of this invention is to provide a novel and improved device and method of detecting the position of an apical constriction in a simple manner with a high degree of accuracy without fear of radiation damage as in the case of the radiographic method.

This invention is based upon the principle that, when the root canal is filled with a suitable electrolyte solution, such as an aqueous solution of common salt, and a fixed voltage or current is applied across the pillar of solution in the root canal, current density and, therefore, potential gradient should vary along the axis of the root canal due to variation of the inner diameter thereof. Accordingly, the device of this invention includes first electrode means which is to be put in contact with the mucous membrane of the oral cavity, second electrode means which is to be put in a decayed opening of the tooth, and means for applying a fixed voltage or current between the first and second electrode means. The device further includes third electrode means which is to be inserted movably into the root canal, and means of detecting potential gradient at the tip of the third electrode means.

Other features and operation of the device of this invention will be described in more detail hereinunder with reference to the accompanying drawings.

IN THE DRAWINGS

FIG. 3 is a cross-sectional side view representing an embodiment of the electrode stylet used in the device of FIG. 1;

FIG. 4 is a cross-sectional view of the electrode stylet of FIG. 3 taken along the line IV—IV thereof;

FIG. 5 is a cross-sectional side view representing another embodiment of the electrode stylet used in the device of FIG. 1;

FIG. 6 is a cross-sectional view of the electrode stylet of FIG. 5 taken along line VI—VI thereof;

Throughout the drawings, like reference numerals are used to denote corresponding structural components.

Figure 1:
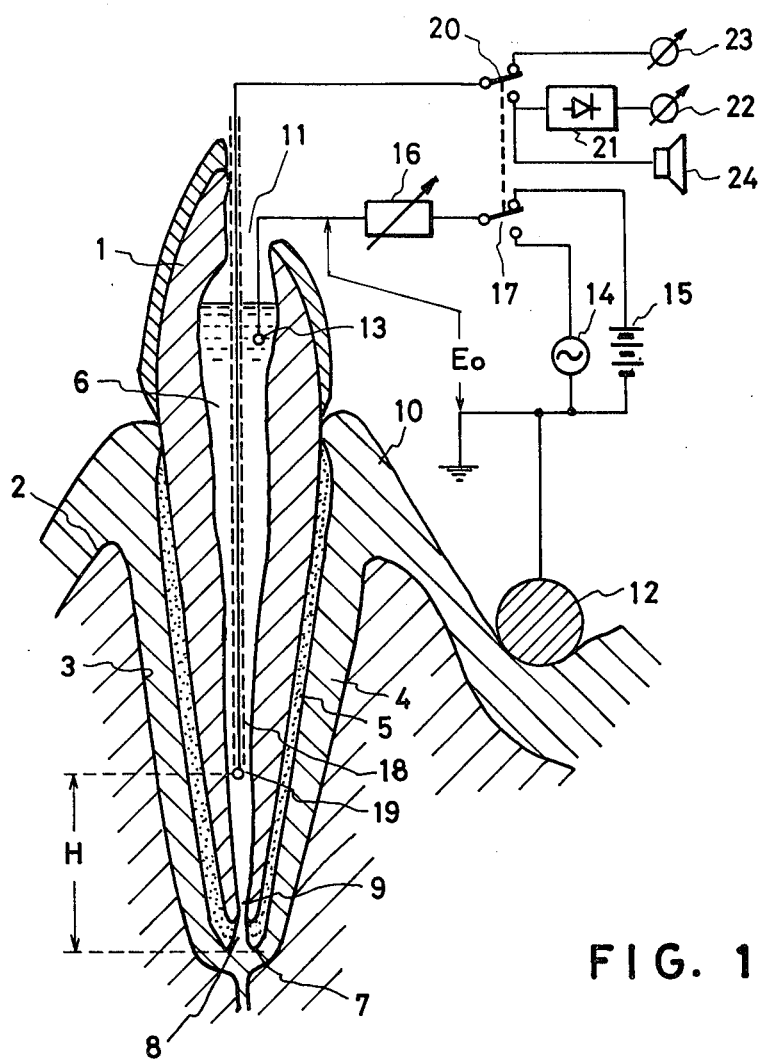
FIG. 1 is a schematic diagram representing an embodiment of the device according to this invention.

Referring to FIG. 1, a decayed tooth 1 is supported in a dental socket 3 of the jaw bone 2 through periodontium 4 and cementum 5, and includes a root canal 6 in the center, which contains dental pulp. The root canal 6 opens in the vicinity of the apical end 7 of the tooth 1 as an apical foramen 8 in the dental socket 3, and an apical constriction 9 lies generally in a position slightly above the opening of the root canal 6. The gum 10 consists of gingiva connecting with the periodontium 4 and mucous membrane which covers the gingiva. The numeral 11 denotes an opening formed by etching or decay.

In the case of detecting the apical constriction 9 with the device of this invention, 0.9% aqueous solution of common salt is first filled into the opening 11 and root canal 6, and a suitable grounded electrode 12 is put in contact with the gum 10 as shown. In practice, a saliva ejector may be used conveniently for this purpose. Another suitable electrode 13, which will be described later, is inserted into the root canal 6 from the decayed opening 11 and also connected through a suitable current control circuit 16, change-over switch 17 and AC source 14 or DC source 15 to the grounded electrode 12. When voltage $E_0$ is applied between the electrodes 12 and 13, most of the current flows from electrode 13, through the root canal 6, apical foramen 8, dental socket 3, jaw bone 2, periodontium 4 and gingiva to the electrode 12, since the dentine and tooth enamel of the tooth 1 exhibit extremely high electric resistance.

Moreover, a probe electrode stylet 19 having an insulating coating on the whole surface thereof except for the tip portion is also inserted into the root canal 6 and connected through a change-over switch 20 interlocked with the switch 17 to a voltmeter 22 accompanied with a rectifier 21 for AC or to a voltmeter 23 for DC.

Figure 2:
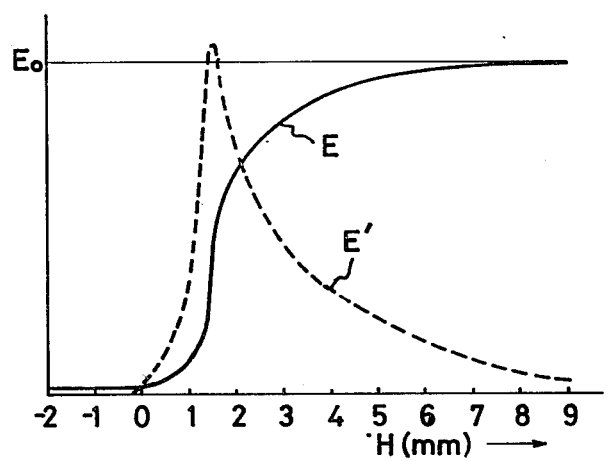
FIG. 2 is a characteristic diagram presented as an aid in explaining the operation of the device of this invention.

When the switches 17 and 20 are set to either AC or DC and and electrode stylet 19 is moved up and down, electric potential indicated by the voltmeter 22 or 23 is plotted as shown by the curve E in FIG. 2, with respect to the distance H between the apical end 7 and the tip of the stylet 19. Curve E' of FIG. 2 represents potential gradient along the root canal 6, which is derived from curve E. While, in this example, the maximum potential gradient is found at height H of about 1.5 millimeters from the apical end 7, it has been confirmed that this is the height of apical constriction 9 of the tooth 1. Thus, the position of the apical constriction can be distinguished with sudden change of indication of the voltmeter 22 or 23. If a speaker 24 is coupled to the AC detection circuit, the apical constriction can be detected as a sudden change of sound volume and this may be more convenient for the operator.

In general, electric resistance of the tissue between the electrodes 12 and 13 is 5 to 7 killo-ohms and electric resistance of the tissue between the electrodes 12 and 19 is several hundred ohms when the electrode 19 is at the apical end 7. The AC or DC voltage $E_0$ applied between the electrodes 12 and 13 is preferably in the order of several millivolts.

FIGS. 3 and 4 show an embodiment of the electrode stylet 19 of FIG. 1, which is composed of a relatively thick body portion 25 and a relatively thin insert leg portion 26. Both portions 25 and 26 are coated with an insulating coating 18 of insulating varnish, for example, except the tip portion 27 and the upper portion of the body portion 25. The body portion 25 is about 1 millimeter in diameter and about 20 millimeters in length, the insert leg portion 26 is about 0.15 millimeters in diameter and about 30 millimeters in length, and the insulating coating 18 is about 10 micro-meters in thickness, for instance.

FIGS. 5 and 6 show another embodiment of the stylet, in which the electrodes 13 and 19 of FIG. 1 are united. Both electrodes are formed in a shape of a probe stylet, the insert leg portions 26 and 29 of which are worked to have flat semicircular cross-sections of about 0.15×0.07 millimeters, for example. The electrode stylets 13 and 19 are coated with insulating coatings 18, separately, as in the case of the embodiment of FIGS. 3 and 4, and both insert leg portions 26 and 29 are bonded together with an adhesive agent 30. The tip 27 of the electrode 19 for measurement extends beyond the tip 32 of the electrode 13 for voltage application by about 3 to 5 millimeters and the insulating coatings 18 of the tips 27 and 32 are stripped off by about one millimeter. The body portion 28 of the electrode 13 is made shorter than the body portion 25 of the electrode 19 for ease of distinction.

This type of combined electrode stylet provides curves E and E' somewhat deviating from those of FIG. 2 since the electrode 13 is not fixed but moves with the electrode 19. However, it is sufficient for attaining the intended object since the peak of curve E' is unchanged. It should be understood that this combined stylet is more convenient for practical use than the aforementioned separate electrodes.

While, in the above-described embodiment of FIG. 1, the potential gradient distribution along the root canal 6 is determined by measuring electric potential along it, a similar result can be obtained by measuring potential difference across a small axial segment of the root canal 6 over its whole length. An embodiment based upon this form of the invention is shown in FIG. 7.

Figure 7:
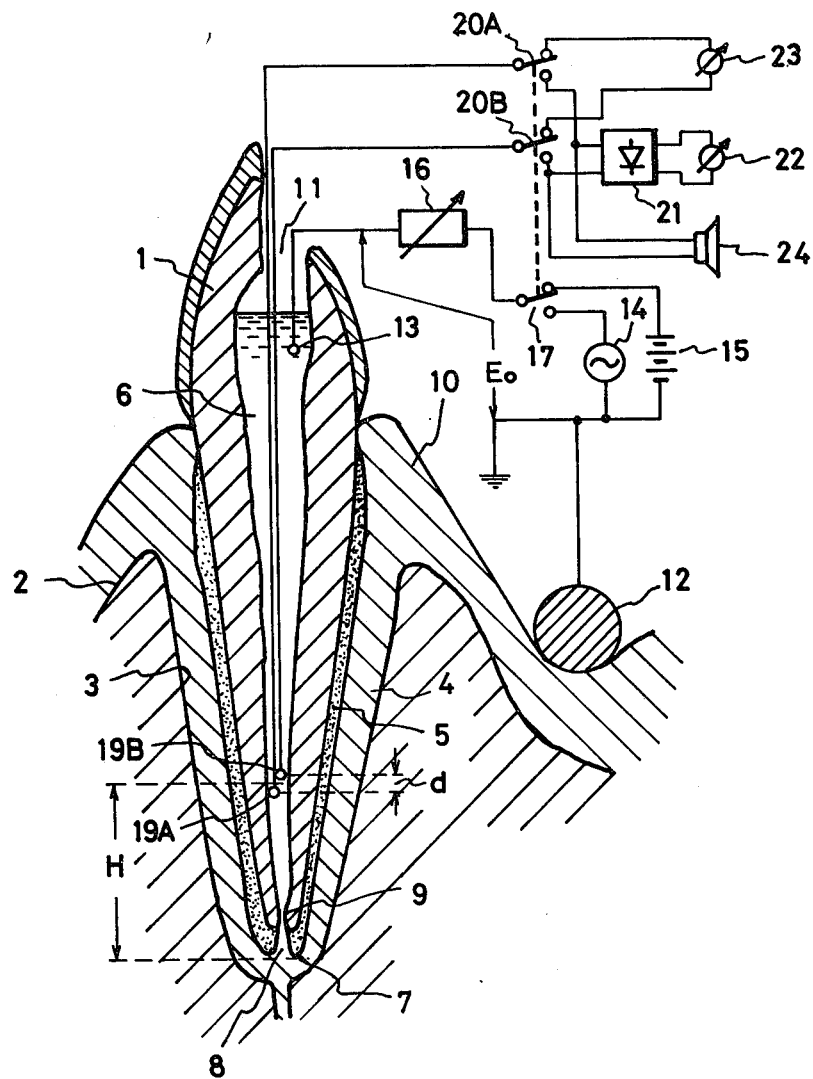
FIG. 7 is a schematic diagram representing a second embodiment of the device according to this invention.

The embodiment of FIG. 7 is the same as the embodiment of FIG. 1 except that the measuring electrode 19 is divided into two parts 19A and 19B, both tips of which are maintained at a predetermined offset d, and voltage appearing between both electrode parts 19A and 19B is measured by the voltmeter 22 or 23. When the pair of electrodes 19A and 19B are moved up and down keeping the offset d unchanged and the measured voltage is plotted with respect to the height H, a curve which is similar to curve E' of FIG. 2 is obtained, since the measured voltage is indicative of the potential gradient at the position of offset d of the electrodes 19A and 19B. Accordingly, in this embodiment, the indication of the voltmeter 22 or 23 and the sound volume of the speaker 24 are peaked when the offset portion is at the apical constriction 9 and lowered on both sides thereof. This feature should sometimes be more convenient for the operator than that of the embodiment of FIG. 1 in which the measured voltage reaches its minimum at the apital constriction and does not change substantially after passing it toward the apical end 7.

In this case, also, voltage $E_0$ applied between the electrodes 12 and 13 may be several millivolts. The offset length d between the tips of electrodes 19A and 19B may be about 0.3 to 0.6 millimeters, in general.

Figure 8:
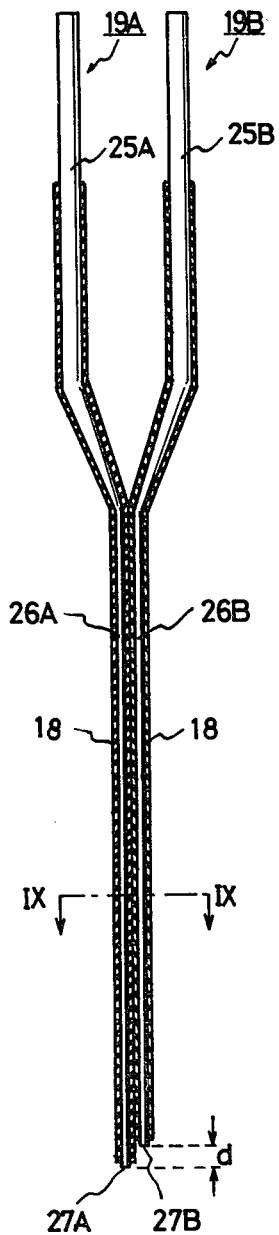
FIG. 8 is a cross-sectional side view representing an embodiment of the electrode stylet used in the device of FIG. 7.
Figure 9:
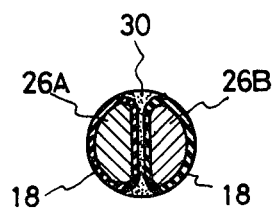
FIG. 9 is a cross-sectional view of the electrode stylet of FIG. 8 taken along the line IX—IX thereof.

FIGS. 8 and 9 show an embodiment of the combined pair of electrodes 19A and 19B. As in the embodiment of FIGS. 3 and 4, both electrodes 19A and 19B are composed of relatively thick body portions 25A and 26B, which are about one millimeter in diameter and about 20 millimeters in length, and relatively thin insert leg portions 26A and 26B, which are about 30 millimeters in length, respectively. The leg portions 26A and 26B are formed to have flat semicircular cross-sections of about 0.15×0.07 millimeters. Both electrodes are coated with an insulating coating 18 in the same manner as aforementioned and both tips 27A and 27B are exposed by stripping off the coatings. Then both leg portions 26A and 26B are bonded together with an adhesive agent 30, keeping the predetermined offset d between the tips 27A and 27B.

Figure 11:
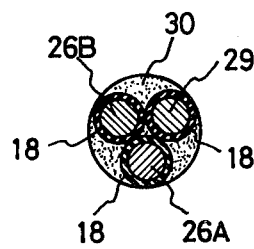
FIG. 11 is a cross-sectional view of the electrode stylet of FIG. 10 taken along the line XI—XI thereof.
Figure 10:
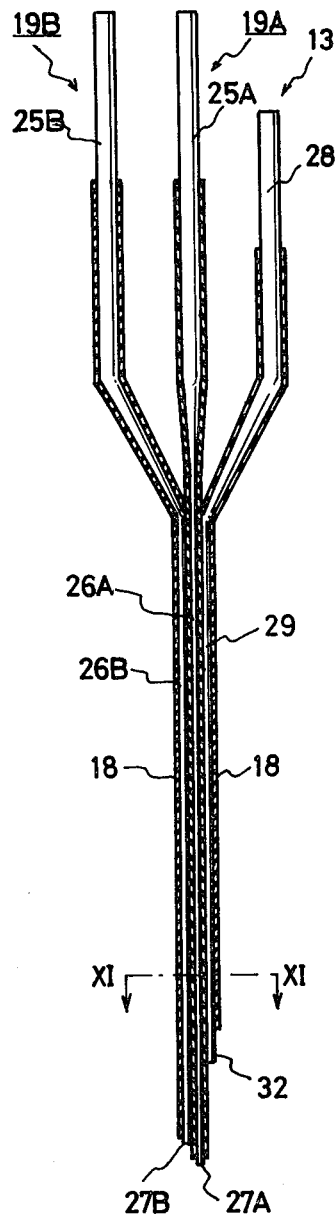
FIG. 10 is a cross-sectional side view representing another embodiment of the electrode stylet used in the device of FIG. 7.

FIGS. 10 and 11 show a further embodiment of the combined electrode stylet, which corresponds to the embodiment of FIGS. 5 and 6, and in which three electrodes 19A, 19B and 13 are bundled together. The electrodes 19A, 19B and 13 are respectively composed of relatively thick body portions 25A, 25B and 28, which are about one millimeter in diameter and about 20 millimeters in length, and relatively thin insert leg portions 26A, 26B and 29, which are about 0.08 millimeters in diametr and about 30 millimeters in length. These electrodes are coated with insulating coatings in the same manner as aforementioned and then bonded together with an adhesive agent 30 by their insert leg portions. In this form of the invention, the body portion 28 of the electrode 13 for voltage application is made slightly shorter than the others for ease of distinction, and the leg portion of the electrode 13 is made shorter than the others by about 3 to 5 millimeters. The coatings 18 of the leg portions 26A and 26B are stripped off only at their tips 27A and 27B, while the tip 32 of the leg portion 29 is stripped of its coating 18 by about one millimeter. As in the embodiment of FIGS. 8 and 9, an offset of about 0.3 to 0.6 millimeters is provided between the tips 27A and 27B of the electrodes 19A and 19B.

As in the case of the embodiment of FIGS. 5 and 6, the voltage applying electrode 13 moves with the measuring electrodes 19A and 19B and the resultant potential gradient distribution deviates slightly from that obtained by the stylet of FIGS. 8 and 9. However, this combined stylet can be used satisfactorily since the position of the peak of potential gradient is unchanged.

As described above, according to this invention, the apical constriction can be easily and distinctly detected by merely inserting an electrode stylet into the root canal and visually and/or audibly indicating the peak of the potential gradient, in a safe and economical fashion.

It should be noted that the above description has been made only for illustration and various modifications and changes can be made by those skilled in the art within the scope of this invention as defined in the appended claims. For example, though a fixed voltage was applied between the first and second electrodes in the above description, it is possible and sometimes more advantageous to provide a fixed current therebetween from a constant current source. In this case, also, the same result as shown in and described in connection with FIG. 2 could be obtained with all types of electrode stylets as shown. An advantage of the fixed current type measurement over the fixed voltage type measurement is that approximate inner diameter of the root canal at various positions can be found from the magnitude of measured voltage when the offset distance of the third electrode of FIG. 8 or 10 is kept constant. The magnitude of the fixed current may be 10 microamperes, r.m.s., for example. Moreover, in the embodiments of FIGS. 5 and 10, the coating 18 of the second electrode stylet is not always necessary. The second electrode may be a simple bare metal wire, such as steel wire.

What is claimed is:

1. A device for detecting the apical constriction in the root canal of a tooth having an electrolyte therein, comprising first electrode means for contacting the mucous membrane in the oral cavity, said first electrode means being coupled to a reference potential point, second electrode means for inserting in said root canal, means coupled to said first and second electrode means for applying a fixed voltage or current therebetween, third electrode means for inserting movably into said root canal, and means coupled to said third electrode means for detecting the potential gradient along said root canal.

2. The device, according to claim 1, wherein said third electrode means comprises a single stylet having an insulation coating thereon with a portion thereof stripped off at the tip, and said potential gradient detecting means includes means for indicating the potential difference between said first and third electrode means.

3. The device, according to claim 2, wherein said second electrode means comprises a single stylet bonded together with said third electrode means side by side with a predetermined offset between the tips thereof.

4. The device, according to claim 2, wherein said second electrode means comprises a single stylet having an insulation coating thereon with a portion thereof stripped off at the tip, and said second and third electrode means are bonded together side by side with a predetermined offset between the tips thereof.

5. The device, according to claim 1, wherein said third electrode means comprises a pair of stylets coated with insulation coating, respectively, portions of which are stripped off at the tips, said pair of electrodes being bonded together side by side with a predetermined offset between said stripped tips, and said potential gradient detecting means includes means for indicating potential difference between said pair of stylets.

6. The device, according to claim 5, wherein said second electrode means comprises a single stylet bonded together with said pair of third electrode means side by side with a predetermined offset between the tips of said second electrode means and said pair of third electrode means.

7. The device, according to claim 6, wherein said second electrode means comprises a single stylet having an insulation coating thereon which is stripped off at the tip.

8. A method of detecting the apical constriction of the root canal of a tooth, comprising the steps of removing the dental pulp from said root canal, filling said root canal with electrolyte solution, putting first electrode means in contact with a mucous membrane in the oral cavity, putting second electrode means in said root canal, providing fixed voltage or current between said first and second electrode means, inserting third electrode means into said root canal and moving the same along said root canal to detect potential gradient distribution along said root canal.

9. The method, according to claim 8, wherein said electrolyte solution is aqueous solution of common salt.

* * * * *